United States Patent

Ezaki et al.

[11] Patent Number: 5,904,967
[45] Date of Patent: May 18, 1999

[54] PUNCTURE RESISTANT MEDICAL MATERIAL

[75] Inventors: Yuzo Ezaki; Yuuki Kobarai; Takahiro Tanigawa; Kouichi Fujita, all of Kanagawa, Japan

[73] Assignee: Terumo Kabushiki Kaisha, Tokyo, Japan

[21] Appl. No.: 08/637,478

[22] Filed: Apr. 25, 1996

[30] Foreign Application Priority Data

Apr. 27, 1995 [JP] Japan ..................................... 7-103507
Jun. 8, 1995 [JP] Japan ..................................... 7-142110

[51] Int. Cl.⁶ .................................................. B29D 22/00
[52] U.S. Cl. .................................... 428/36.92; 428/36.91; 428/36.9; 428/522; 428/515; 138/118; 138/137; 138/141; 623/1
[58] Field of Search ..................... 428/522, 515, 428/911, 912, 36.9, 36.91, 36.92; 138/118, 137, 141; 623/1; 524/570, 571, 575, 379

[56] References Cited

U.S. PATENT DOCUMENTS

| | | | |
|---|---|---|---|
| 4,216,803 | 8/1980 | Hall | 138/144 |
| 5,411,550 | 5/1995 | Herweck et al. | 623/1 |
| 5,459,174 | 10/1995 | Merrill et al. | 522/35 |
| 5,549,664 | 8/1996 | Hirata et al. | 623/1 |
| 5,628,782 | 5/1997 | Myers et al. | 623/1 |

FOREIGN PATENT DOCUMENTS

| | | |
|---|---|---|
| B-53-2186 | 1/1978 | Japan . |
| A-6-80856 | 3/1994 | Japan . |
| 2 016 482 | 9/1979 | United Kingdom . |
| WO 93/23093 | 11/1993 | WIPO . |

OTHER PUBLICATIONS

Patent Abstracts of Japan, vol. 096, No. 010, Oct. 31, 1996 & JP 08 164197 A, Jun. 25, 1996.

Database WPI, Section Ch, Week 9342, Derwent Publications Ltd., Class A18 XP002065710 & JP 05237163 A, Feb. 28, 1992.

Database WPI, Section Ch, Week 9508, Derwent Publications Ltd., Calss A96 XP002065711 & JP 06335514 A, May 28, 1993.

*Primary Examiner*—José G. Dees
*Assistant Examiner*—Michael A. Williamson
*Attorney, Agent, or Firm*—Burns, Doane, Swecker & Mathis, LLP

[57] ABSTRACT

A highly puncture resistant, biocompatible medical material is provided. The medical material may be used for a dialysis graft or an artificial blood vessel. The medical material has a puncture resistant layer comprising a resin prepared by mixing 100 parts by weight of a styrene elastomer and/or an olefin elastomer, and at least 20 parts by weight of an isoprene derivative.

6 Claims, 1 Drawing Sheet

PUNCTURE RESISTANT MEDICAL MATERIAL

BACKGROUND OF THE INVENTION

This invention relates a medical material having excellent puncture resistance and biocompatibility which is adapted for use at a site of repeated puncture with a medical needle. More specifically, this invention relates to a puncture resistant, biocompatible tubular structure such as an artificial medical material.

Some medical materials are repeatedly punctured by a medical needle, and kept in contact with a body tissue. A sheet of polyurethane or silicone rubber; a knitted or woven fabric or a felt of Dacron®; a stretched sheet or a felt of Teflon®; and the like have been used for such medical materials.

Such medical materials, however, suffered from insufficient puncture resistance as well as biocompatibility, and as a consequence, various unfavorable problems occurred by the use of such medical material at a site where the material was kept in a prolonged contact with a body tissue.

In hemodialysis, an interior shunt is usually formed by anastomosing an artery with a vein. Such a shunt, however, can not be formed when the patient has a damaged artery or vein. In such case, an artificial blood vessel prepared from Teflon® has been implanted at the corresponding site. Such an artificial blood vessel, however, suffered from various problems after prolonged use and repeated puncture with a medical needle. The insufficient puncture resistance of such an artificial blood vessel resulted in blood leakage upon anastomosis and after repeated puncture with the medical needle, and such blood leakage resulted in bacterial infection, formation of ulcer, chronic inflammation, formation or bump and hematoma, calcification, and the like. The conventional artificial blood vessel also suffered from difference in physical properties with the host blood vessel to which it is anastomosed, and such difference often resulted in the thickening of the blood vessel at the site of the anastomosis.

SUMMARY OF THE INVENTION

In view of such situation, an object of the present invention is to provide a medical material adapted for use at a site where frequent access with blood is required. More particularly, an object of the present invention is to provide an artificial blood vessel which has an excellent puncture resistance to endure repeated puncture by a medical needle such as a puncture needle or an indwelling needle as well as a good compatibility with both the native blood vessel to be anastomosed therewith and the surrounding tissue.

The embodiments of the present invention are given below by way of example, and not by way of limitation.

(1) A puncture resistant medical material having
   a puncture resistant layer comprising a resin prepared by mixing 100 parts by weight of a styrene elastomer and/or an olefin elastomer, and at least 20 parts by weight of an isoprene derivative.

(2) A puncture resistant medical material comprising
   a puncture resistant layer comprising a resin prepared by mixing of a styrene elastomer and/or an olefin elastomer, and at least 20 parts by weight of an isoprene derivative; and
   a layer of an olefin elastomer nonwoven fabric disposed on the puncture resistant layer.

(3) A puncture resistant tubular laminate structure comprising
   a puncture resistant layer comprising a resin prepared by mixing of a styrene elastomer and/or an olefin elastomer, and at least 20 parts by weight of an isoprene derivative; and
   a layer of an olefin elastomer nonwoven fabric disposed on the puncture resistant layer on its outer surface.

(4) An artificial blood vessel comprising
   a puncture resistant non-porous layer comprising a resin prepared by mixing 100 parts by weight of a styrene elastomer and/or an olefin elastomer, and at least 20 parts by weight of an isoprene derivative;
   a porous layer of a polyester resin disposed on the puncture resistant layer on its inner surface; and
   a porous layer disposed on the puncture resistant layer on its outer surface.

(5) An artificial blood vessel according to the above (4) wherein
   the inner porous polyester layer comprises a woven, knitted, or braided fiber structure of a polyethylene terephthalate/polybuthylene terephthalate conjugate fiber;
   the puncture resistant layer comprises a resin prepared by mixing 100 parts by weight of a styrene elastomer and at least 20 parts by weight of an isoprene derivative; and
   the outer porous layer comprises an olefin elastomer nonwoven fabric.

DETAILED DESCRIPTION OF THE INVENTION

The medical material of the present invention has a puncture resistant layer comprising a resin prepared from 100 parts by weight of a styrene elastomer and/or an olefin elastomer, and at least 20 parts by weight of an isoprene derivative. The puncture resistant layer usually constitutes an intermediate layer or an inner layer when the medical material is in the form of implant. However, it is no problem that the puncture resistant layer constitutes an outer layer for use the medical materials which are repeatedly punctured by a medical needle.

The medical material of the present invention may be used for a medical device that is kept in contact with the body tissue for a prolonged period, for example, an artificial blood vessel for a dialysis graft or the like, prosthesis, IIS port, implanted artificial heart and catheter for its power supply, shunt, and patch. The medical material may be efficiently used by forming into a form suitable for such device. Therefore, the form of the medical material is not limited to any particular form. However, it is preferably in the form of a tube comprising a two-layer or three-layer laminate.

Figure 1:
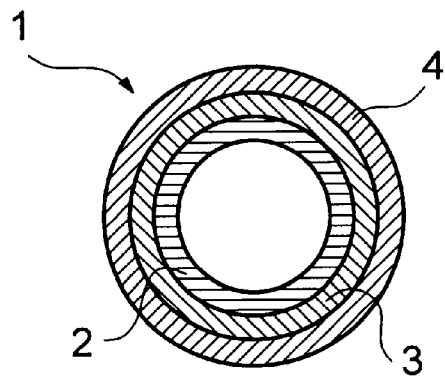
FIG. 1 is a schematic cross-sectional view of an artificial blood vessel according to an embodiment of the present invention.

FIG. 1 shows an embodiment wherein the medical material of the present invention constitutes an artificial blood vessel 1 comprising a porous inner layer 2, a non-porous puncture resistant intermediate layer 3, and a porous outer layer 4. The artificial blood vessel of the present invention may generally have an inner diameter in the range of from 3 mm to 10 mm. The inner layer 2 may have a thickness of from about 50 μm to about 500 μm. The intermediate puncture resistant layer 3 will have a higher puncture resistance if the layer is thick. The intermediate layer 3, however, may generally have a thickness of from about 0.1 to about 0.5 mm, and the layer of such thickness will endure repeated puncture by a normal medical needle. The outer layer 4 will have a higher susceptibility for tissue invasion if the layer is thick. The outer layer 4, however, may have a thickness of from about 50 μm to about 500 μm. The inner layer 2, the puncture resistant layer 3, and the outer layer 4 may be adhered with each other either by means of a binder or by fusion with heat. Adhesion by heat fusion is preferable in terms of safely.

Figure 2:
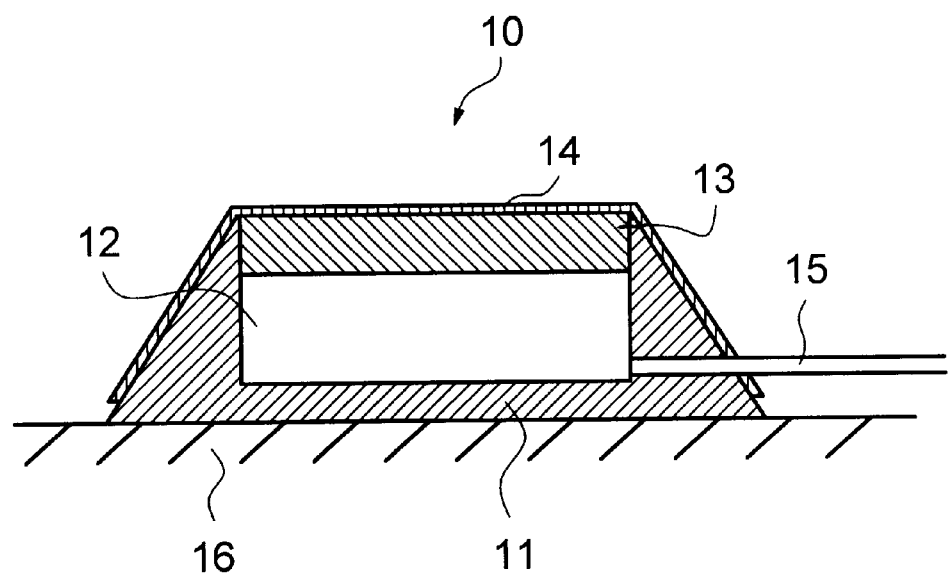
FIG. 2 is a schematic cross-sectional view of a IIS drug solution port according to an embodiment of the present invention.

FIG. 2 is a cross-sectional view of an IIS drug solution port 10 disposed in contact with a human body 16. Alternatively, the IIS drug solution port 10 may be embedded in the human body 16. The IIS drug solution port 10 comprises a main structure 11 comprising a polyeter sulfone or the like, which is disposed in contact with the human body 16, and a drug solution reservoir 12 is defined within the main structure 11. The drug solution reservoir 12 is covered on the other side, namely, on the side remote from the human body 16, with the medical material of the present invention in sheet form. The medical material of the present invention used in this embodiment comprises a bilayer laminate comprising a non-porous puncture resistant layer 13 and a polyethylene terephthalate/polybuthylene terephthalate layer 14. The polyethylene terephthalate/polybuthylene terephthalate layer 14 comprises a knitted or woven structure of polyethylene terephthalate/polybuthylene terephthalate conjugate fiber. The drug solution reservoir 12 is in communication with the exterior of the IIS drug solution port 10 via a conduit 15 extending through the wall of the main structure 11. The IIS drug solution port 10 having the structure as described above is a medical device used when a frequent parenteral administration or infusion of a drug or a solution is required, for example, upon (1) peritoneal dialysis and (2) administration of a carcinostatic agent. In the peritoneal dialysis, the conduit 15 is inserted in the abdominal cavity for introduction of the dialysis solution into the abdominal cavity. In the administration of a carcinostatic agent, the conduit 15 is connected with the liver artery or the like.

As described above, the medical material of the present invention has a puncture resistant layer comprising a resin prepared from 100 parts by weight of a styrene elastomer and/or an olefin elastomer, and at least 20 parts by weight of an isoprene derivative. Such layer has a high elasticity as well as an excellent puncture resistance to endure repeated puncture by puncture needle or indwelling needle. Such layer, when laminated to form an artificial blood vessel, will prevent blood leakage upon implantation by anastomosis with the host blood vessel or repeated puncture with a medical needle.

The styrene elastomer which may be used for the puncture resistant layer of the present medical material may be the one primarily comprising a copolymer constituted from a moiety based on styrene and/or ethylene and a moiety comprising butadiene and/or isoprene and/or hydrogenation product thereof. Exemplary commercially available styrene elastomers of such type include Krayton®, Califlex® (Shell Chemical), Tufprene®, Tuftek® (Asahi Chemical Industry Co., Ltd.), Aron AR (Aron Chemical Industry Co., Ltd.), Rabalon® (Mitsubishi Petrochemical Co., Ltd.), JSR-TR, JSR-SIS, Dynalon (Japan Synthetic Rubber Co., Ltd.), and Septon (Kuraray Co., Ltd.), The olefin elastomer which may be used for the puncture resistant layer of the present medical material may comprise a copolymer of ethylene and propylene, or a copolymer further comprising third comonomer of α-olefin or diene. Exemplary commercially available olefin elastomers of such type include Milastomer, Tafmer® (Mitsui Petrochemical Industries Co., Ltd.), Sumitomo TPE (Sumitomo Chemical Industries Co., Ltd.) and Thermorun® (Mitsubishi Petrochemical Co., Ltd.).

When 20 parts by weight or more of an isoprene derivative is added to 100 parts by weight of the styrene elastomer and/or the olefin elastomer, the resulting resin will have a reduced hardness, and an improved tensile strength. Preferable isoprene derivatives for use in the present invention are squalane and squalene although the isoprene derivatives used are not limited to any particular species. The squalane and squalene used may be the one that has been isolated or derived from a natural source or the one that has been synthesized. Other isoprene derivatives that may be used in the present invention include geranyl geranate, geranyl geraniol, geranyl linalool, isophyitol, phytol, phytyl acetate, hexahydropharnicyl acetone, pharnicyl acetone, nerolydol, pharnecene, bisabolene, bisabolol, pharnesol, gephalnate, pharnesal, phalnecyl acid, geranyl acetone, pseudoionone, α-Ionone, β-Ionone, α-methylionone, and γ-methylionone. These isoprene derivatives are metabolyzable in the human body via routine metabolic pathway, and therefore, the isoprene derivative that erroneously bled out of the medical material and absorbed in the human body will be readily metabolized. Therefore, use of such isoprene derivatives is preferred in terms of safely.

The puncture resistant layer of the medical material is non-porous, and may be produced by forming the resin material as described above into a sheet form by any of the conventional processes, for example, by using a heat press machine. When the puncture resistant layer of a tubular structure is required, the thus formed sheet-form layer may be wound around a core bar and heat-treated to form a tubular structure, or alternatively, the resin material may be directly formed in to a tubular structure by extrusion or compression.

The most preferable puncture resistant layer used in the present invention is in the form of a sheet prepared by a conventional method from the resin material comprising 100 parts by weight of a styrene elastomer and from 20 to 1000 part by weight, and preferably, from 20 to 200 parts by weight of an isoprene derivative. A thickness in the range of from about 0.1 to about 0.5 mm is sufficient for the required puncture resistance although the puncture resistance will increase with the increase in its thickness.

Styrene elastomers are thermoplastic, and can be fabricated in heat molten gel state at a temperature at which the isoprene derivative is not denatured. Such feature of the styrene elastomer is in good contrast with the thermosetting silicone rubber which permits no further fabrication once the resin has cured. When the puncture resistant layer is fabricated from a styrene elastomer, the once formed tubular structure may be re-fabricated to alter the inner diameter of a particular section of the tubular structure, for example, by inserting a rod with a diameter slightly larger than the inner diameter of the tubular structure, and heating and cooling the tubular structure under the dilated conditions. A silicone rubber may also be fabricated into a tubular structure of the same configuration. In the case of a silicone rubber, however, the resin must be fabricated into the final configuration at once since the silicone rubber cannot be subsequently re-fabricated.

Use of a styrene elastomer for the puncture resistant layer has another merit that the finished article can be further shaped into the desired contour. More illustratively, an artificial blood vessel product fabricated by using a styrene elastomer for the puncture resistant layer can be re-heated and bent into an artificial blood vessel of desired contour, for example, immediately before the operation after confirming the condition of the implantation site. Such an artificial blood vessel in a bent form can be fabricated from a silicone rubber only if the final bent contour were determined before the production.

The safety of the isoprene derivative-containing styrene elastomer used in the present invention has been confirmed in a subcutaneous implantation test of one year. Among the isoprene derivatives, squalane is the one widely used in cosmetic product. Squalane is a substance formed by saturating the double bond in squalene by hydrogen addition, and squalene is a sebaceous component. Accordingly, the puncture resistant layer of the present invention comprising the styrene elastomer and the squalane is highly safe when applied in human.

The outer layer of the medical material according to the present invention may comprise a non-limited material. The outer layer, however, may preferably comprise an olefin elastomer similar to the one used for the puncture resistant layer. Exemplary such olefin elastomers are Milastomer and Toughmer manufactured by Mitsui Petrochemical Industries, Ltd. The outer layer may comprise a porous structure, and may comprise a knitted, woven, or braided porous structure or a non-woven fabric. Most preferably, the outer layer may comprise a non-woven fabric of an olefin elastomer, which is a safe, non-inflammatory material suffering from little bleeding. This material also permits a quick invasion of the surrounding fibroblast cells into the fabric, resulting in the improved styptic effect after the puncture. The non-woven fabric of an olefin elastomer may be fabricated by any of the conventional processes such as spun bond process, melt blowing process, flash spinning process, and carding process, and the fiber constituting the non-woven fabric may have a diameter of from 0.1 $\mu$m to 100 $\mu$m, and preferably, from 1 $\mu$m to 20 $\mu$m. The non-woven fabric with the fiber diameter of less than 0.1 $\mu$m may be insufficient in strength, and the non-woven fabric with the fiber diameter in excess of 100 $\mu$m is too rigid to contact with the tissue, and is likely to physically induce an inflammation. The thickness of the outer layer may preferably be as thin as possible so long as the layer allows the invasion of the surrounding tissue. Such thickness is from 0.1 mm to 0.5 mm.

The medical material of the present invention may optionally have a porous layer in the interior of the puncture resistant layer. The porous layer becomes in contact with the blood, and may preferably comprise a polyester resin porous layer.

The provision of the polyester porous layer in the interior of the puncture resistant layer will improve the pressure resisting strength of the medical material, and at the same time, promote the formation of the new internal membrane thereon. The polyester resins which may be used for such layer include polyethylene terephthalate (PET), polybuthylene terephthalate (PBT), a polyester-polyether block copolymer, and a polyester-polyester block copolymer. The polyester porous layer in the interior of the puncture resistant layer may comprise a knitted, woven, or braided fiber structure of a polyester resin fiber such as warp-knitted fabric, weft-knitted fabric, triaxially knitted fabric, braid of such resin fiber, or a combination thereof. The polyester porous layer is not limited to such structure, and may also comprise a fibrous structure wherein a space is defined between fibers and a non-woven fabric. The porous layer may also comprise a porous structure produced by stretching process wherein said polyester resin is molded into a desired shape, and then subjected to heat treatment, stretching, and additional heat treatment to form a porous structure; or a porous produced by solvent extraction process wherein said polyester resin is molded with a filler, and the filler is extracted by dissolution with an appropriate solvent to thereby leave a porous structure.

When the polyester porous layer in the interior of the puncture resistant layer is formed from a polyester resin fiber, the fiber used is not limited to a monofilament fiber, and a conjugate fiber produced by simultaneously spinning two or more types of the polyester resins at once may also be used. The process by which the conjugate fiber is produced is not limited to any particular process, and the conjugate fiber used may be a side-side conjugate fiber (wherein two ore more components are conjugated side by side), a sheath-core fiber (wherein one component serving the core is surrounded by another component), a multi-sheath-core fiber (wherein two or more cores constituted from one component is surrounded by another component), a multi-layer conjugate fiber (wherein the two component are alternately conjugated to form a laminate). Among such conjugate fibers, the preferred is the side-side conjugate fiber in view of elasticity and elastic recovery. The fiber may preferably be the one that has been improved for elastic recovery, and the fiber may preferably be imparted with latent crimpability after the formation of the fiber in view of the stabilization of the porous layer. In the present invention, the polyester porous layer in the interior of the puncture resistant layer may preferably comprise a knitted, woven, or braided fiber structure of a side-side conjugate fiber produced by simultaneously spinning polyethylene terephthalate and polybuthylene terephthalate.

When the polyester porous layer in the interior of the puncture resistant layer is formed from a polyester resin fiber, the fiber used may preferably be a textured fiber. The texturing may be conducted by any of the known processes such as a process wherein the fiber is twisted, heat set, and untwisted; a false twist process wherein the fiber is continuously twisted, heat set, and untwisted; a forced-feed process wherein the fiber is forced-fed into a space of a predetermined volume and then pulled out with simultaneous heat treatment; an abrasion process wherein the fiber is heated and rubbed with each other; air jet process wherein the fiber is ejected with a high-temperature, high-pressure air jet and crimped by collision; and a shaping process wherein the fiber is passed through a pair of heated gears to impart the contour of the gear to the fiber.

The polyester resin fiber as described above may generally have a thickness of from 20 to 150 denier, preferably from 20 to 75 denier, and most preferably from 20 to 50 denier. When the polyester resin fiber is in excess of 150 denier, the porous layer formed therefrom would be excessively thick to loose the softness. The polyester resin fiber finer than 20 denier will result in an insufficient strength of the resulting porous layer.

The puncture resistant medical material of the present invention in the form of a sheet or a tube may optionally comprise one or more additional layers in addition to the layers as described above. Exemplary such additional layers are a layer comprising a highly biocompatible material and a layer comprising a material having a high physical strength.

The layers of the medical material may be adhered with each other either by means of a binder or by fusion with heat. Adhesion by heat fusion is preferable for safely.

The present invention is further described by referring to the Examples and Comparative Examples, which by no means limit the scope of the present invention.

EXAMPLES

Preparation of sheet (Sheet A)

100 g of a styrene elastomer (Toughprene, manufactured by Asahi Chemical Industry Co., Ltd.) and 20 g of squalane (manufactured by Kuraray Co., Ltd.) were placed in a beaker, and the mixture was thoroughly stirred with a spoon. The mixture was allowed to stand overnight for aging, and then, mixed for 3 minutes with a mixing roll (manufacture by Etoh Seisakusho) at 160° C. The mixture was pressed into a sheet (A) of 0.4 mm thick by a hot press machine (manufacture by Etoh Seisakusho) at 160° C.

Preparation of nonwoven fabric (Nonwoven fabric B)

An olefin elastomer (Milastomer, manufactured by Mitsui Petrochemical Industries, Ltd.) was injected from a hot melt applicator system (nozzle: HMG-19-UF, manufactured by Nordson K.K.) to form a nonwoven fabric (B) with a thickness of 0.2 mm comprising the thin fiber with a diameter of from about 10 to 15 μm.

Preparation of tube (Tube G)

An elastic conjugate fiber of side-side type comprising polyethylene terephthalate and polybuthylene terephthalate (a conjugate fiber with a resin weight ratio of 50:50, 30 denier/18 filament) was applied to a 30 gauge double Raschel loom to produce a tubular fabric by reverse half knitting. The tubular fabric was turned inside out, and scoured to obtain a tube (G) having an inner diameter of 4 mm.

Preparation of tube (Tube D)

100 g of a styrene elastomer (Clayton, manufactured by Shell Chemical) and 30 g of squalane (manufactured by Kuraray Co., Ltd.) were mixed by repeating the procedure described in the preparation of sheet (A), and the mixture was applied to an extruder to produce a tube (D) having an inner diameter of 5 mm and a length of 6 cm.

The thus prepared materials were used for the production of artificial blood vessels of the present invention and artificial blood vessels for comparison purpose.

(a) Artificial blood vessel 1 (ABV GAB) Tube (G) was wound with sheet (A), and heated in an oven at 120° C. for 5 minutes. Subsequently, nonwoven fabric (B) was wound over the sheet (A), and heated in an oven at 120° C. for 5 minutes for thermal adhesion to thereby obtain an artificial blood vessel 1 (ABV GAB) according to the present invention.

(b) Artificial blood vessel 2 (ABV GDB)

Tube (G) was inserted in tube (D), and the tube (D) was further wound with nonwoven fabric (B). The tubular assembly was heated in an oven at 120° C. for 5 minutes for thermal adhesion to thereby obtain artificial blood vessel 2 (ABV GDB) according to the present invention.

(C) Artificial blood vessel 3 (ABV DB)

Tube (D) was further wound with nonwoven fabric (B). The tubular assembly was heated in an oven at 120° C. for 5 minutes for thermal adhesion to thereby obtain artificial blood vessel 3 (ABV DB) according to the present invention.

(d) Artificial blood vessel 4 (ABV AB)

Sheet (A) was shaped annular tube having inner diameter 5 mm×length 60 mm, and further overlaid with nonwoven fabric (B), and heated in an oven at 120° C. for 5 minutes for thermal adhesion to thereby obtain artificial blood vessel 4 (ABV AB) according to the present invention.

Comparative Examples

Artificial blood vessels 1 to 4 for comparison purpose were also prepared by similar procedure.

Tube (Tube Si)

Tube (Si) was prepared from a two part silicone resin (Silastics, manufactured by Dow-Corning).

Comparative artificial blood vessel 1 (ABV SiT)

Tube (Si) was wound with a Tetron felt (T) (manufactured by Medox) and heated to obtain comparative artificial blood vessel 1 (ABV SiT).

Comparative artificial blood vessel 2 (ABV SiD')

Tube (Si) was wound with a Dacron felt (D') (manufactured by Medox) and heated to obtain comparative artificial blood vessel 2 (ABV SiD').

Comparative artificial blood vessel 3 (ABV DT)

Tube (D) was wound with a Tetron felt (T) (manufactured by Medox) and heated to obtain comparative artificial blood vessel 3 (ABV DT).

Comparative artificial blood vessel 4 (ABV DD')

Tube (D) was wound with a Dacron felt (D') (manufactured by Medox) and heated to obtain comparative artificial blood vessel 4 (ABV DD').

Comparative artificial blood vessel 5 (Dialysis graft)

A dialysis graft manufactured by Gore-Tex comprising Teflon one layer was used as comparative artificial blood vessel 5.

The thus prepared artificial blood vessels of the present invention and the comparative artificial blood vessels for comparison purpose were evaluated by the tests as described below.

Test 1: Water leakage test

Puncture resistance was evaluated in terms of water leakage by introducing water into the artificial blood vessel at a flow rate of 200 ml/min and at a pressure of 120 mmHg, and the artificial blood vessel was punctured for ten times with a 17 gauge AFV needle (manufactured by Terumo Corporation). The artificial blood vessels used were artificial blood vessel 3 of the present invention and artificial blood vessel 5 for comparison purpose, which is a dialysis graft. The artificial blood vessel 3 of the present invention exhibited an improved puncture resistance with a water leakage of 12.0 ml/min, when compared with the artificial blood vessel 5 for comparison purpose which showed a water leakage of 92.0 ml/min.

Test 2: In vivo blood leakage and biocompatibility

The artificial blood vessels of the present invention and the artificial blood vessels for comparison purpose were respectively anastomosed to the femoral artery of a dog. The artificial blood vessel was punctured with the 17 gauge needle at ten times/day and one day/week to observe the degree of blood leakage. The implanted artificial blood vessel was taken out after 3 months, and the surrounding tissue was observed to evaluate the degree of healing. The results are shown in Table 1.

TABLE 1

Results of Animal Experiments

|  | Blood leakage after puncture with 17G needle | Binding with surrounding tissue |
|---|---|---|
| Examples |  |  |
| ABV 1 (GAB) | No | good |

TABLE 1-continued

Results of Animal Experiments

|  | Blood leakage after puncture with 17G needle | Binding with surrounding tissue |
| --- | --- | --- |
| ABV 2 (GDB) | No | good |
| ABV 3 (DB) | No | good |
| ABV 4 (AB) | No | good |
| Comparative Examples |  |  |
| Tube (D) | No | not detected |
| Tube (Si) | Yes** | not detected |
| ABV 1 (SiT) | Yes** | poor* |
| ABV 2 (SiD') | Yes** | poor* |
| ABV 3 (DT) | No | poor* |
| ABV 4 (DD') | No | poor* |
| ABV 5 (Dialysis graft) | No | not detected |

ABV: artificial blood vessel
*chronic inflammation was observed.
**heavy leakage In test 2, artificial blood vessel 3 of the present invention showed no blood clotting in its interior, and instead, formation of the new internal membrane was observed. In the artificial blood vessel for comparison purpose, formation of the new internal membrane was limited to the site of anastomosis with the host blood vessel.

On the exterior of the comparative artificial blood vessels 1 to 4, a strong inflammatory reaction involving foreign body giant cell was observed in the Dacron felt or the Tetron felt layer. In contrast, on the exterior of the artificial blood vessel 3 of the present invention, a significant invasion by fibroblast as well as collagen production were noticed in the nonwoven fabric layer, indicating the favorable restoration of the tissue.

EFFECTS OF THE INVENTION

The puncture resistant medical material of the present invention is excellent in puncture resistance and biocompatibility, and therefore, such material may be advantageously used for such medical device as artificial blood vessel for dialysis shunt, IIS port, and implanted artificial heart and catheter for energy delivery thereto.

The artificial blood vessel of the present invention has a puncture resistant layer comprising the resin prepared by mixing 100 parts by weight of the styrene elastomer and/or the olefin elastomer, and at least 20 parts by weight of the isoprene derivative, and therefore, the artificial blood vessel is highly resistant to blood leakage. The artificial blood vessel of the present invention is also provided with the layer the olefin elastomer nonwoven fabric on its exterior, and therefore, it has an improved binding ability with the surrounding tissue. The artificial blood vessel of the present invention is optionally provided with a polyester resin porous layer on its interior, and therefore, the artificial blood vessel can endure a high pressure and formation of the new internal membrane is promoted. As described above, the artificial blood vessel of the present invention has an excellent puncture resistance to endure repeated puncture by a medical needle such as a puncture needle or an indwelling needle as well as a good compatibility with both the native blood vessel to be anastomosed therewith and the surrounding tissue, and therefore, may be effectively used for such application as dialysis graft.

We claim:

1. A puncture resistant medical material comprising
   a porous inner layer comprising a polyester resin;
   a non-porous puncture resistant intermediate layer dispersed in the inner layer, said puncture resistant layer comprising a resin prepared by mixing 100 parts by weight of at least one moiety selected from the group consisting of a styrene elastomer and an olefin elastomer, and at least 20 parts by weight of an isoprene derivative; and
   an outer layer dispersed on the puncture resistant layer.

2. The puncture resistant medical material according to claim 1 wherein said inner layer comprises a knitted, woven, or braided fiber structure of a conjugate fiber of polyethylene terephthalate and polybuthylene terephthalate; and said outer layer comprises a nonwoven fabric of an olefin elastomer.

3. The puncture resistant medical material according to claim 1 wherein said medical material is an artificial blood vessel.

4. The puncture resistant medical material according to claim 2 wherein said medical material is an artificial blood vessel.

5. An artificial blood vessel which comprises a puncture resistant medical material having a non-porous puncture resistant layer comprising a resin prepared by mixing 100 parts by weight of at least one moiety selected from the group consisting of a sytrene elastomer and an olefin elastomer, and at least 20 parts by weight of an isoprene derivative.

6. The artificial blood vessel according to claim 5, wherein said material has a layer of non-woven fabric comprising an olefin elastomer disposed on said puncture resistant layer.

* * * * *